United States Patent [19]
Pasch et al.

[11] Patent Number: 5,746,721
[45] Date of Patent: May 5, 1998

[54] PULSED LAVAGE PUMP WITH INTEGRAL POWER SOURCE AND VARIABLE FLOW CONTROL

[75] Inventors: Kenneth A. Pasch, Kennebunkport, Me.; Andrew Zeigler, Arlington, Mass.

[73] Assignee: C.R. Bard, Inc., Murray Hill, N.J.

[21] Appl. No.: 389,155

[22] Filed: Feb. 15, 1995

[51] Int. Cl.$^6$ ........................................................ A61H 9/00
[52] U.S. Cl. ........................... 604/153; 604/152; 604/151
[58] Field of Search ..................................... 604/131, 132, 604/151, 152, 153, 154; 606/154, 161, 160; 417/218, 219, 220, 221

[56] References Cited

U.S. PATENT DOCUMENTS

| | | |
|---|---|---|
| 1,227,164 | 5/1917 | Manly . |
| 1,989,117 | 1/1935 | Svenson . |
| 2,048,524 | 7/1936 | Svenson . |
| 2,115,121 | 4/1938 | Phillips . |
| 2,348,679 | 5/1944 | Groves . |
| 2,356,993 | 8/1944 | Glasner et al. . |
| 2,393,175 | 1/1946 | Laskey . |
| 2,406,115 | 8/1946 | Stephan . |
| 2,539,277 | 1/1951 | Schroepfer . |
| 2,737,896 | 3/1956 | Neyer . |
| 2,795,968 | 6/1957 | Eriksson . |
| 2,856,793 | 10/1958 | Budlong . |
| 2,921,529 | 1/1960 | Bennett . |
| 3,073,178 | 1/1963 | Barnes et al. . |
| 3,073,418 | 1/1963 | Bentley . |
| 3,119,280 | 1/1964 | Mann et al. . |
| 3,155,141 | 11/1964 | Doyle et al. . |
| 3,205,725 | 9/1965 | Uhtenwoldt . |
| 4,231,724 | 11/1980 | Hope et al. . |
| 4,282,867 | 8/1981 | Du Toit . |
| 4,299,221 | 11/1981 | Phillips et al. . |
| 4,569,674 | 2/1986 | Phillips et al. . |
| 4,621,566 | 11/1986 | Johnson et al. . |
| 4,655,690 | 4/1987 | Boedecker et al. . |
| 4,655,754 | 4/1987 | Richmond et al. . |
| 4,662,829 | 5/1987 | Nehring . |
| 4,826,494 | 5/1989 | Richmond et al. . |
| 4,890,340 | 1/1990 | Lovitt . |
| 4,930,997 | 6/1990 | Bennett . |
| 5,019,038 | 5/1991 | Linden . |
| 5,097,540 | 3/1992 | Lovitt . |
| 5,193,986 | 3/1993 | Grant et al. . |
| 5,195,959 | 3/1993 | Smith . |
| 5,230,704 | 7/1993 | Moberg et al. . |
| 5,246,367 | 9/1993 | Ito et al. . |
| 5,269,750 | 12/1993 | Grulke et al. . |
| 5,281,108 | 1/1994 | Brooke . |
| 5,282,787 | 2/1994 | Wortrich . |
| 5,335,855 | 8/1994 | Borod . |
| 5,360,338 | 11/1994 | Waggoner . |
| 5,368,569 | 11/1994 | Sanese . |

FOREIGN PATENT DOCUMENTS 0329599  8/1989  European Pat. Off. .

OTHER PUBLICATIONS

Patent Abstracts of Japan, vol. 005, No. 037 (M-058), 10 Mar. 1981 &JP, A, 55 161659 (Ricoh Co. Ltd.), 16 Dec. 1980.

*Primary Examiner*—Sam Rimell
*Attorney, Agent, or Firm*—Bookstein & Kudirka, P.C.

[57] ABSTRACT

A self contained pulsatile surgical irrigation device that includes a housing, a trigger moveably connected to the housing, a motor within the housing, a pump within the housing, and a mechanical drive train for coupling the motor to the pump. The trigger is mechanically connected to the drive train to enable the stroke of the pump to be varied, thereby varying the output flow from the device.

19 Claims, 7 Drawing Sheets

5,746,721

PULSED LAVAGE PUMP WITH INTEGRAL POWER SOURCE AND VARIABLE FLOW CONTROL

FIELD OF THE INVENTION

This invention relates to a pulsed lavage device usable in a surgical environment to deliver irrigation liquid to a surgical site.

BACKGROUND OF THE INVENTION

It is important during surgical procedures to maintain the operative site clear of debris and to maintain the site clean and antiseptic. Among the common techniques for maintaining a clean surgical site is to irrigate the site with an irrigation or antiseptic solution. Typically, the liquid is supplied from a reservoir through tubing to a dispensing handle that is manipulated by the surgeon or a surgical assistant. Removal of the irrigation liquid as well as other fluids may collect at the surgical site is effected by applying a suction instrument in the region.

A number of irrigation devices have been used and proposed. Generally, they incorporate an arrangement for developing and delivering the liquid in a pulsatile manner. The pulsatile flow is high efficient in dislodging debris. The effectiveness of the pulsating fluid technique is the result of the repeated flexure of tissue and/or repeated dynamic impact from the pulsations which tend to materially assist in working loose of dirt particles and other debris. In general, it has been considered desirable to be able to control the fluid delivery as to volume, pulsating frequency and impacting force of the liquid on the tissue, etc. It is desirable to be able to vary the characteristics of the emitted fluid stream to accommodate specific surgical or wound cleaning requirements. For example, the nature of the tissue in the surgical site may require a more gentle or a more forceful liquid flow. Among the systems employed in the prior art include those that are powered by external energy sources, including electrically and pneumatically driven pumps. Some systems employ complex controls to vary.

It would be desirable to provide an entirely self-contained powered pulsatile pump having the ability to vary the flow rate and pressure of the irrigating liquid yet which is constructed to be of low cost so that the device may be disposed of after a single use. It is among the general objects of the invention to provide such an improved surgical irrigation device.

SUMMARY OF THE INVENTION

The invention is used in connection with a source of irrigation liquid such as a reservoir that may be hung overhead on an I.V. pole. The device includes tubing that is connectible directly to the reservoir, as by a spike at the end of the tubing. The other end of the tubing is connected to a handpiece that is held and controlled by the physician or a surgical assistant. In accordance with the invention, all of the components for pumping and controlling the fluid are contained within the handpiece. Those components include a battery, an electric motor, a linear stroke pump and a drive mechanism that connects the motor to the pump. The handpiece includes a trigger that, in turn, controls three functions of the device including turning the motor on and off, controlling the drive mechanism in a manner that varies the effective pumping stroke of the pump and effecting a shut-off for liquid flow to assure that the device will not leak when the trigger is released. The construction, including the control mechanism, is such that the device, in its entirety, is of low cost and is readily disposable after a single use.

The linear stroke pump may be in the form of a bellows having a fixed end connected to a valve housing that controls the one-way flow of fluid and a movable opposite end. The movable end is reciprocated by an eccentric drive mechanism including a crank and connecting rod. The crank is rotatable about an axis and the effective length of the bellows stroke is determined by the location of the crank rotational axis with respect to the bellows. The axis is permitted a limited amount of movement in a direction perpendicular to the axis and generally parallel to the bellows axis. The extent of that movement can be varied from zero, at which the axis does not move and a limited amount in which some movement is permitted. When the axis is maintained in a fixed position, the full amount of the stroke effected by the crank mechanism is transmitted to the bellows with a resultant maximum flow output. When the crank axis is permitted some limited movement, the extent of the effective stroke of the bellows is reduced by an amount corresponding to the amount of movement permitted the crank axis. The trigger controlled mechanism is provided to control the extent to which limited translational movement of the crank axis is permitted.

It is among the general objects of the invention to provide an improved self-powered disposable pulsed irrigation device for use in a medical environment.

Another object of the invention is to provide a device of the type described that is highly efficient yet is of low cost and lends itself to disposable use.

A further object of the invention is to provide a device of the type described that incorporates a pump mechanism that operates with a linear stroke and in which a simple trigger-controlled mechanism is provided to control variation in the effective stroke of the pump and the flow characteristics of the emitted liquid.

Another object of the invention is to provide a self-contained device of the type described that is ready to use simply by connecting the tubing directly to the source of irrigation liquid.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
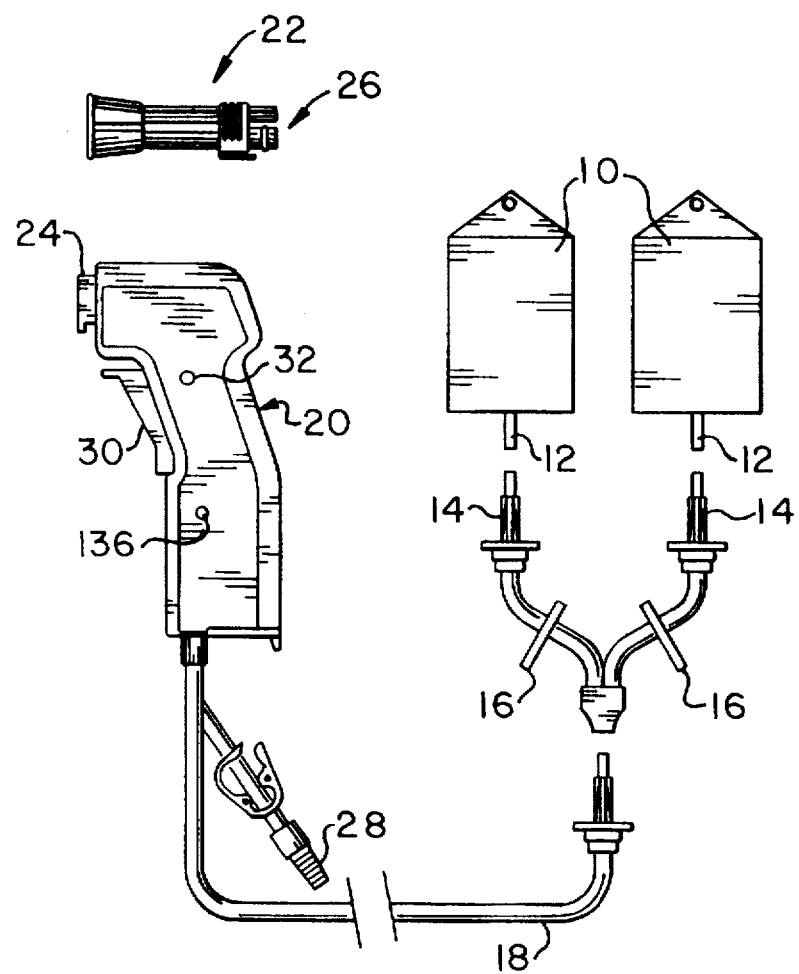
FIG. 1 is a schematic illustration of an irrigation system in accordance with the invention.

As shown in FIG. 1, the irrigation system includes a reservoir of irrigation liquid (e.g., saline), such as one or more bags 10 containing the liquid. The reservoir preferably is adapted to be suspended overhead, as from an I.V. pole, in order to create a gravity pressure head that can facilitate flow of liquid through the system. Each irrigation bag 10 has an outlet port 12 adapted to receive a spike adapter 14 on an end of the flexible tubing to connect the tubing to the irrigation bags 10. Clamps 16 may be provided at various locations along the tubing to control the flow through the tubing. In accordance with the present invention, the device includes a liquid delivery tube 18 that is connectible, at one end, either directly or indirectly to the irrigation bags 10 and, at the other end, to a handpiece 20. The handpiece 20 contains the entire pump mechanism, power source and control system for controlling the outlet flow of irrigation liquid from the handpiece. The handpiece may be somewhat pistol shaped and has a connector socket 24 at its outlet end to which the proximal end of a combined irrigation/suction wand 22 may be detachably connected. The wand 22 also includes a suction tube that is connectible to a suction conduit that extends through the handpiece 20 and emerges at its lower end, terminating at a suction tube connection 28 that is connectible to a suction source. The handpiece includes a trigger 30 that, when squeezed, closes electrical contacts to initiate operation of the motor to drive the pump. The trigger also is coupled to an internal mechanism by which the output of the pump can be controlled. Progressive squeezing of the trigger results in progressively increased flow of irrigation liquid. A trigger lock 32 is provided to enable the physician to lock the trigger in its fully depressed configuration thereby maintaining maximum liquid flow without requiring continued squeezing on the trigger. A lock pin 34 is provided to secure the trigger and internal components in a selected position to facilitate sterilization and initial operation of the device, as will be described.

Figure 2:
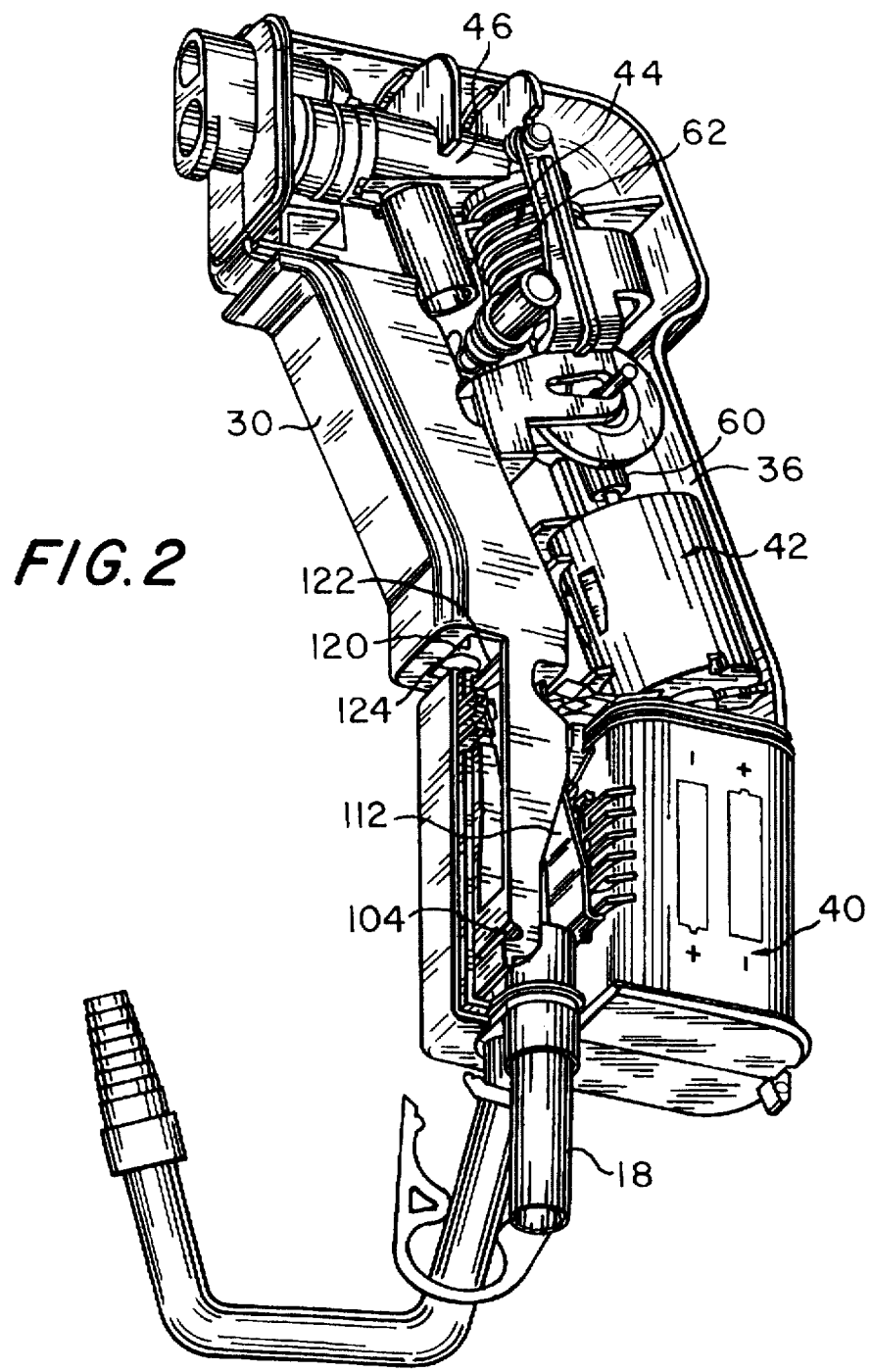
FIG. 2 is an illustration of the handpiece with half of the cover removed to illustrate its interior components.
Figure 3:
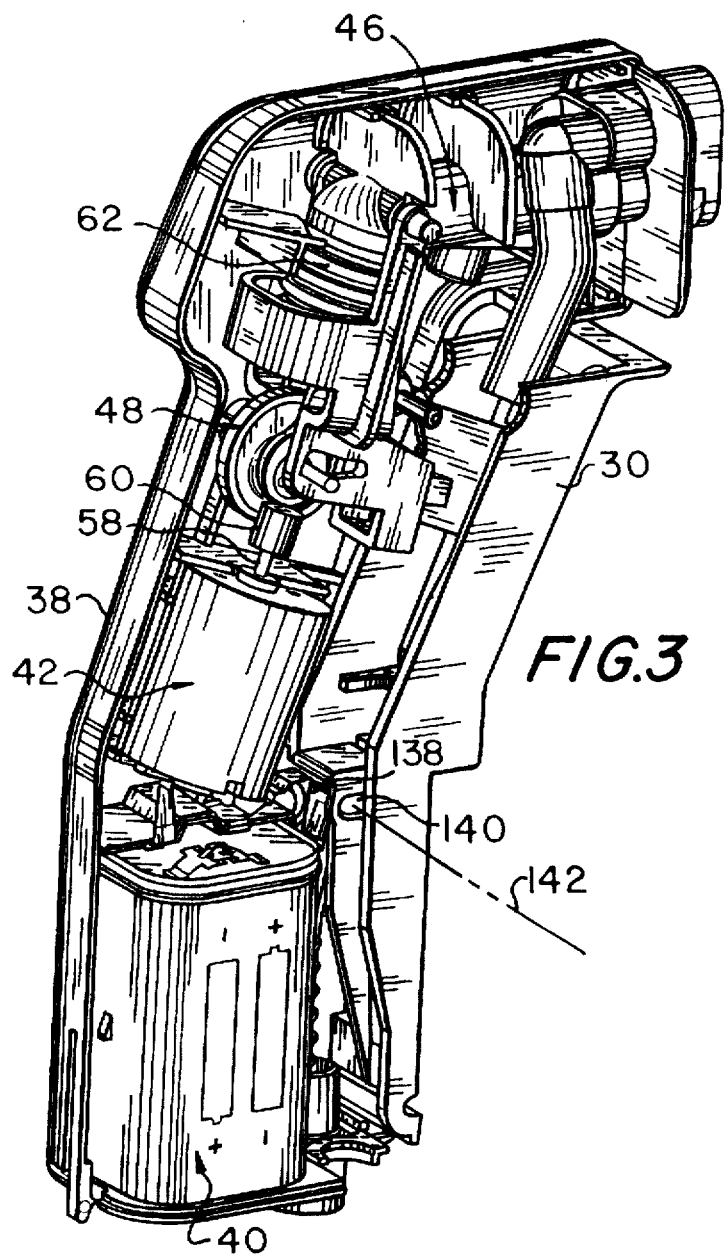
FIG. 3 is an illustration of the handpiece similar to FIG. 2 as seen from the other side of the handpiece and with the cover on the other side removed.

FIGS. 2 and 3 illustrate the internal assembly of the components of the handpiece. The handpiece includes a housing that may be formed from a pair of mateable molded housing sides 36, 38. The interior surface of the housing sides 36, 38, may be formed with various internal projections, walls, sockets and the like to capture securely the internal components as required. The components include a battery pack 40, a D.C. motor 42, a bellows pump 44 and associated valve housing 46 and a drive mechanism 48 that operatively connects the motor 42 to the bellows pump to effect a linear reciprocating operation of the bellows. The drive mechanism 48 is constructed to be controlled by a trigger 30 in a manner that varies the effective pumping stroke of the bellows pump 44 thereby to control the output of irrigation liquid. Operation of the trigger 30 also controls the switch that connects and disconnects the battery and motor 42. The trigger 30 also is configured so that when released, the fluid flow line through the handpiece 20 is pinched closed to preclude inadvertent leakage of irrigation liquid from the device.

The self-contained battery pack 40 includes a battery case 52 that contains four size AA batteries sufficient to drive the D.C. motor 42. The battery case 52, with loaded batteries, is insertable into a receptive socket 54 (FIG. 4) defined within the lower end of the handpiece 20. A flexible latching arrangement may be formed integrally with the housing to secure the battery case 52 in place. The latch mechanism may be constructed to enable the batteries to be removed from the device after the device has been used so that the batteries can be disposed of separately. Electrical contacts are disposed in the handpiece housing and are associated with the batteries and the motor 42 to effect electrical connection between the two. That connection normally is open and is closed when the trigger 30 is depressed.

The motor 42 is a D.C. motor and is preferably selected so that it can be operated to effectively operate the pump mechanism being powered by four AA batteries. The motor 42 includes an output shaft 58 that carries a pinion gear 60. When the motor 42 is operated, the pinion gear 60 drives the drive mechanism 48, as described in further detail below.

Figure 6:
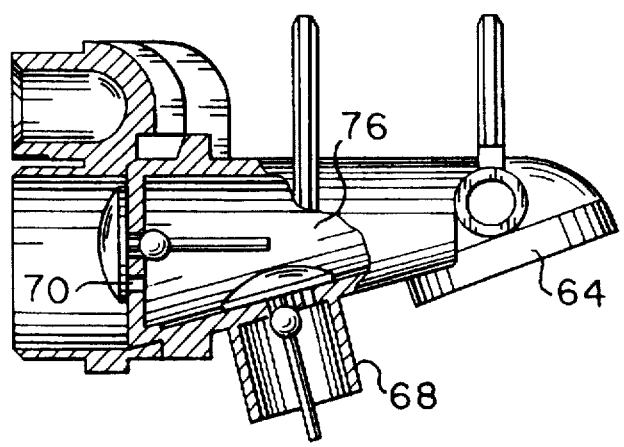
FIG. 6 is a sectional illustration of the valve housing and valve arrangement by which unidirectional flow of irrigation liquid is maintained.

The pump itself incorporates a linear reciprocating stroke and preferably is in the form of a flexible bellows 62. One end of the bellows 62 is securely attached to a port 64 (see FIGS. 6A, 6B and 7) of the valve housing 46. The bellows 62 may be formed from any of a variety of materials including a variety of flexible polymers. The other end of the bellows 62 is movable and is attached to a reciprocating yoke assembly 66 that forms part of the drive mechanism 48. As will be described in further detail, the movement of the yoke assembly 66 can be controlled to vary the effective stroke imparted to the bellows 62. The valve housing 46 also includes an inlet port 68 and an outlet port 70, each of which is provided with an umbrella valve, 72, 74, respectively. The inlet port 68 is connected to a flexible internal tube 69, shown schematically in FIG. 8 that connects to the liquid delivery tube 18. The inlet umbrella valve 72 enables liquid to flow from the reservoir through the tubing 18, 69 and through the inlet umbrella valve 72 into a valve chamber 76. Liquid can flow out of the valve chamber 76 through the outlet umbrella valve 74. As the bellows 62 is reciprocated, the expansion portion of its stroke will cause irrigation liquid to be drawn through the liquid delivery tube 18, the inlet umbrella valve 72 and into the valve chamber 76. When the stroke of the bellows 62 reverses, in a pumping direction, fluid contained within the valve chamber 76 will be ejected through the outlet port 70, past the umbrella valve 74. Continued reciprocation of the bellows 62 will cause repeated pulsating flow through the system and out of the irrigation line of the irrigation/suction wand 22. From the foregoing it will be appreciated that the volume and pressure of liquid that is emitted during each pulsing cycle are dependent on the length of stroke effected by the bellows 62.

The length of the bellows stroke is controlled by the drive mechanism 48 that, in turn, is controlled by the extent to which the trigger 30 is depressed. The yoke assembly 66 includes a pair of parallel connecting arms 78, the end of each terminating in an integral ring 80. The other end of yoke assembly 66 defines a bight 82 formed to define a connector attachable to a button 84 formed integrally with the free end of the bellows 62. The rings 80 on the free ends of the connecting arms 78 are rotatably attached to a corresponding pair of circular bosses 86 formed integrally with and on opposite sides of a circular face gear 88. The face gear 88 is mounted on a transverse shaft 90. The shaft 90 extends through the center of the face gear 88, with the bosses 86 being disposed eccentrically to the transverse shaft axis. The face gear 88 and eccentrically disposed bosses 86 define a crank mechanism. The face gear 88 includes a transversely facing ring of gear teeth 92 that engage and mesh with the teeth on the pinion gear 60 on the motor output shaft 58. The ends of the shaft 90 are rotatably retained in receptive members formed on the inner face of each of the housing halves 36, 38 as described in further detail below. From the foregoing, it will be appreciated that when the motor 42 is driven, the pinion gear 60 drives the face gear 88 and crank mechanism which, in turn, causes the bellows 62 to reciprocate along the bellows axis under the influence of the eccentric crank connection between the yoke assembly 66 and face gear 88.

In accordance with one aspect of the invention, the shaft 90 is supported in a manner that allows the shaft 90 to have limited freedom of motion in a direction perpendicular to the shaft axis and generally parallel to the axis of the bellows 62. Thus, the ends of the shaft 90 are contained in slots 89 defined by a pair of parallel rails 91 formed on the inner face of each of the housing halves 36, 38. The ends of the shaft 90 are contained to enable the shaft 90 to move generally parallel to the axis of the bellows 62. The ends of the rails 91 may be enclosed to define somewhat of an oval-shaped entrapment for the ends of the shaft 90. The extent of such shaft movement is governed by the extent to which the trigger 30 is depressed. The extent to which the shaft 90 is permitted to move can vary from no movement up to a predetermined maximum range of movement. When the shaft 90 is retained in its fixed, no movement position, the full amount of the stroke of the yoke assembly 66 will be transmitted to the bellows 62 and, consequently, will effect the maximum amount of pumping permitted by the system. Conversely, when the transverse shaft 90 is released to permit it to move parallel to the bellows axis, the shaft 90 will oscillate within the permitted range of movement. To the extent that the shaft 90 oscillates, that portion of the stroke is not transmitted to the bellows 62, thus reducing the effective stroke of the bellows 62 with a consequent reduction in flow output.

Figure 7A:
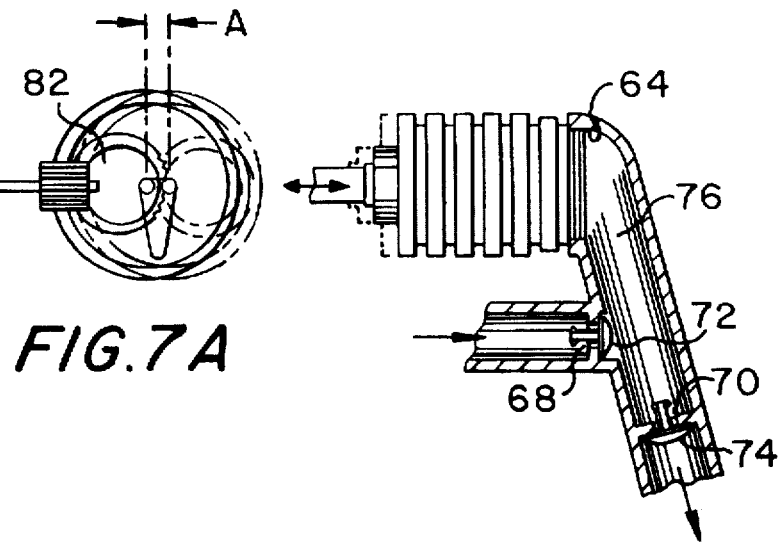
FIG. 7A is a diagrammatic illustration of the mechanism for coupling the motor to the bellows in which the stroke of the bellows is at its minimum.
Figure 7B:
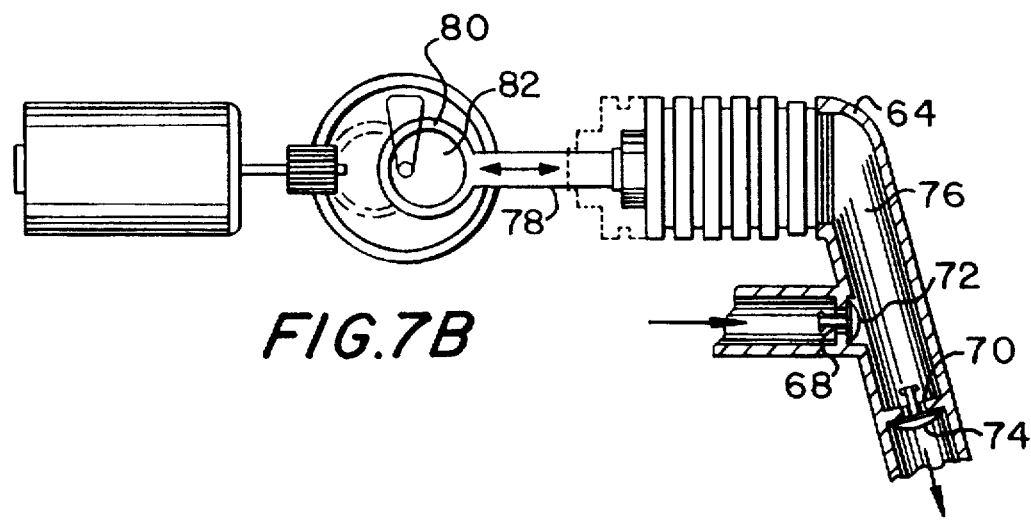
FIG. 7B is an illustration similar to FIG. 7A in which the control mechanism is configured to provide a maximum stroke for the bellows.

The extent to which the shaft 90 is permitted to have limited freedom of movement is governed by a control member 94 illustrated best in FIGS. 5A–5C, 7A and 7B. The control member 94 may be molded in an appropriate plastic and include a pair of pivot arms 96 having pivots 98 formed integrally at one end. The control member 94 preferably is rigidified by a pair of integral cross members 93, 95. The cross member 95 also is configured to include a lug 118 adapted to be engaged by a portion of the trigger 30 so that when the trigger 30 is squeezed, the control member 94 will pivot in a direction that will progressively restrict the freedom of translational movement permitted the shaft 90. The other ends of the pivot arms 96 include an integrally formed control plate 100, the control plates 100 being disposed to embrace the face gear 88 and along a plane essentially perpendicular to the axis of the shaft 90. Each of the control plates 100 is formed to include an elongated slot 102. The lengthwise dimension of each slot 102 extends generally perpendicular to the direction that the guide rails 91 permit translational movement of the shaft 90. The width of each slot 92 diverges from its narrowest end to a wider end. The slots 102 are arranged so that the ends of the shaft 90 can protrude through the slots 102. Thus, the guide rails 91 permit movement of the shaft 90 in a direction generally parallel to the bellows axis and perpendicular to the lengthwise dimension of the slots 102. The extent to which such shaft 90 movement is permitted is controlled by the position of the control slots 102 with respect to the shaft 90. When the control member 94 is pivoted to capture the shaft 90 in its most narrow end, then the cooperation of the slot 102 and guide rails 91 will maintain the shaft 90 in a fixed position so that the full extent of the reciprocating stroke of the drive mechanism 48 can be transmitted fully to the bellows 62. That configuration is achieved when the trigger 30 is fully depressed. Conversely, when the trigger 30 is released, the control member 94 is permitted to move to contain the shaft 90 within a wider portion of the control slot 102. In that wider portion, the shaft 90 can oscillate and, to the extent the shaft 90 oscillates, the stroke imparted to the bellows 62 is reduced. FIGS. 7 and 7A illustrate diagrammatically the manner in which the permitted oscillation of the shaft 90 effects the stroke of the bellows 62. In FIG. 7B the control slot 102 is oriented to capture the shaft 90 and prevent it from oscillatory movement with respect to the housing. Consequently, the face gear 88 is constrained to rotate about a fixed axis and the full extent of the stroke will be transmitted to the bellows 62, as indicated in phantom. In FIG.7A the control slot 102 is disposed with its widest end in alignment with the shaft 90, thereby permitting a range of freedom of movement, as indicated at A. In this configuration, the amount of the stroke imparted to the bellows 62 is reduced by the dimension A and, as indicated in phantom, the effective stroke of the bellows 62 is reduced. Consequently, the flow rate and output of the device similarly is reduced.

The trigger 30 is mounted for pivotal movement within the housing by engagement of a transverse slot 104 formed in the lower end of the trigger 30 that engages a transverse rib 106 (FIG. 4) formed on the inner surface of the lower front wall 108 of the handpiece 20. The trigger 30 is biased normally in an outward configuration, in which the lower portion of the trigger 30 is urged toward the lower front wall 108 of the handpiece 20. The upper portion of the trigger 30 which is graspable by the operator protrudes through an opening defined in the mid to upper region of the front wall. The trigger 30 is biased in this configuration by a leaf spring 112 captured in the lower portion of the housing and bearing against the lower portion of the trigger 30 above the hinge 104. The trigger 30 is connected to the movable end of the control member 94 by an articulated connection between an upstanding inner wall 114 on the trigger 30 and the connecting lug 118 that extends from the freely movable portion of the control member 94. The connecting lug 118 and inner wall 114 are pinned together by a pin and slot connection, including a slot 116 formed in the upstanding wall 114. Thus, when the trigger 30 is squeezed, the articulated connection between the wall 114 and the connecting lug 118 will cause the above-described movement of the control member 94 to control the freedom of movement permitted the transverse crank shaft 90.

An additional function served by the trigger 30 includes an arrangement for pinching off the flexible tubing 69 that communicates the inlet port 68 of the valve housing 46 with the inlet tube fitting at the bottom end of the handpiece. The internal tubing configuration in its relation to the trigger 30 and housing is illustrated diagrammatically in FIG. 8. The trigger 30 includes a surface defining an opening 120 (FIG. 2) through which the tubing (not shown in FIG. 2) can pass. The opening 120 is defined by a forwardly facing edge 122 that faces and opposes a rearwardly facing edge 124 formed on the lower front wall 108 (see also FIG. 4). When the trigger 30 is released, the leaf spring 112 urges the trigger 30 forwardly to cause the flexible internal tube 69 to become pinched between the edges 122, 124. The internal tube 69 is sufficiently flexible in relation to the force developed by the leaf spring 112 so that flow through the internal tube 69 is effectively precluded when the trigger 30 is released. The pinching force should be sufficient to preclude leakage of irrigation liquid through the system under the influence of gravity resulting from the head developed by the overhead reservoir 10. Among the advantages of this arrangement for pinching off the flow through the intermediate conduit is that it relieves the umbrella check valves 72, 74 from having to resist such leaking flow themselves. By transferring all of the shut-off control to the pinching effected by the trigger 30, it is possible to use umbrella valves 72, 74 that have a very low, almost neglible cracking pressure (the pressure necessary to initiate opening of the valve). Thus, when the device is operating the relatively low flow impedance presented by the valves 72, 74 enhances the ability of the device to develop increased flow. Additionally, it enables the use of relatively low cost valving elements.

It may be desirable, in order to reduce fatigue, for the user to lock the trigger 30 in a depressed configuration in order to obtain high flow rates over an extended period of time. To that end, an arrangement is provided for locking the trigger 30 in that depressed configuration. In the illustrative embodiment, the device includes a transverse locking pin 126 having several circular flanges 128. The pin 126 protrudes through an opening 130 formed in a boss integral with the left side of the handpiece. The pin 126 is biased outwardly by a compression spring at 132. When in a normal relaxed configuration, the spring 132 biases the lock pin 126 outwardly in a disengaged position. When it is desired to lock the trigger 30 in a depressed configuration, the trigger 30 is depressed and the pin 126 is then urged inwardly. The ridges 128 of the pin 126 are aligned with a somewhat hooked edge 134 of the upstanding inner wall 114. With the trigger 30 depressed and the locking pin 126 urged inwardly, the trigger 30 then is released to capture the hooked edge 134 between the ridges 128. The trigger 30 then will remain locked in its depressed configuration. Release of the trigger 30 is effected simply by again squeezing on the trigger 30 to free the hooked edge 134 from engagement with the ridges 128 on the pin 126. The compression spring 132 then returns the pin 126 to its relaxed configuration, the trigger 30 having been freed.

Figure 8:
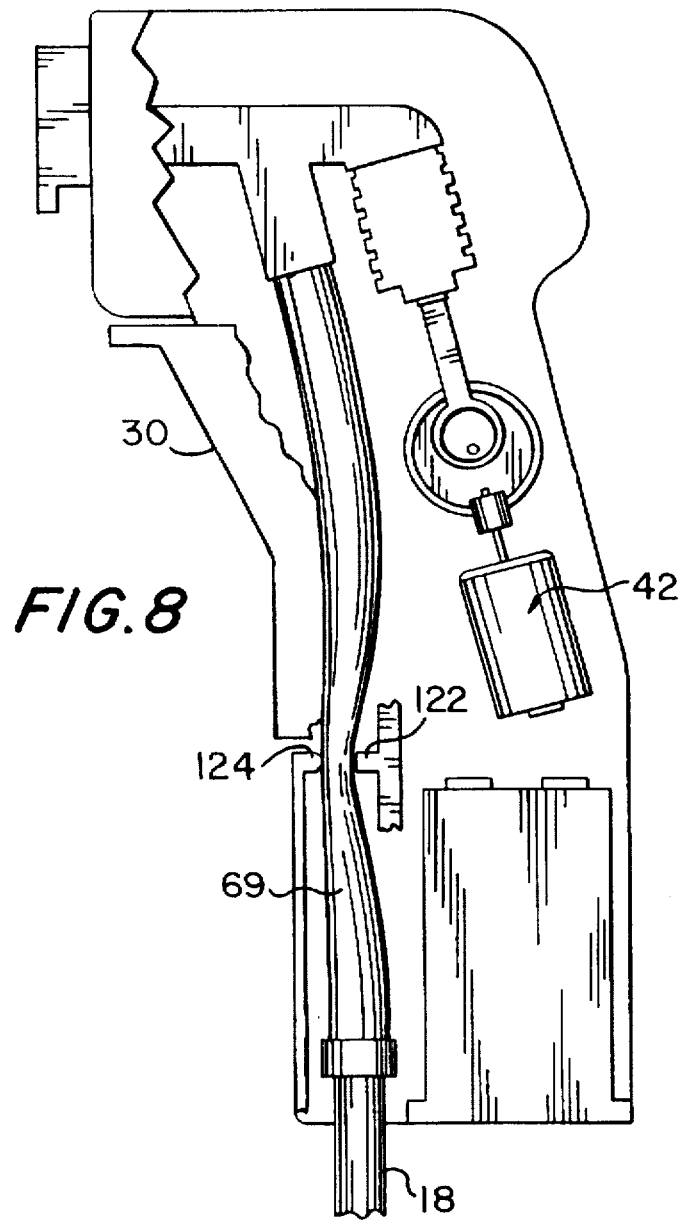
FIG. 8 is a schematic illustration of the manner in which the trigger and housing cooperate to enable shut-off of flow of irrigation fluid.

A further aspect of the invention is illustrated diagrammatically in FIG. 8 in which a second locking arrangement is provided to lock the trigger 30 in a desired relative open configuration as is desirable during initial sterilization as well as to maintain the inner tube open and unkinked during shipment and storage. To that end, a lock pin 136 is provided. The lock pin 136 is inserted through the device through holes formed in the housing sides. The lock pin 130 is aligned with the electrical contacts (schematically in FIG. 8) to maintain the contacts apart when the pin 130 is in place. An aperture is formed in the trigger 30 so that it is alignable for the locking pin 130 when the trigger 30 is in an open configuration. Thus, although the electrical contacts would normally be maintained closed, the locking pin 130, which is formed from a non-conductive material (e.g., plastic) will not cause inadvertent operation of the motor 42 and depletion of the batteries. Simultaneously the flow passage through the internal fluid tube 69 is maintained open so as to avoid kinks during prolonged storage periods and also to assure that during sterilization, the sterilizing medium will contact fully the internal surfaces of the tube 69.

Figure 4:
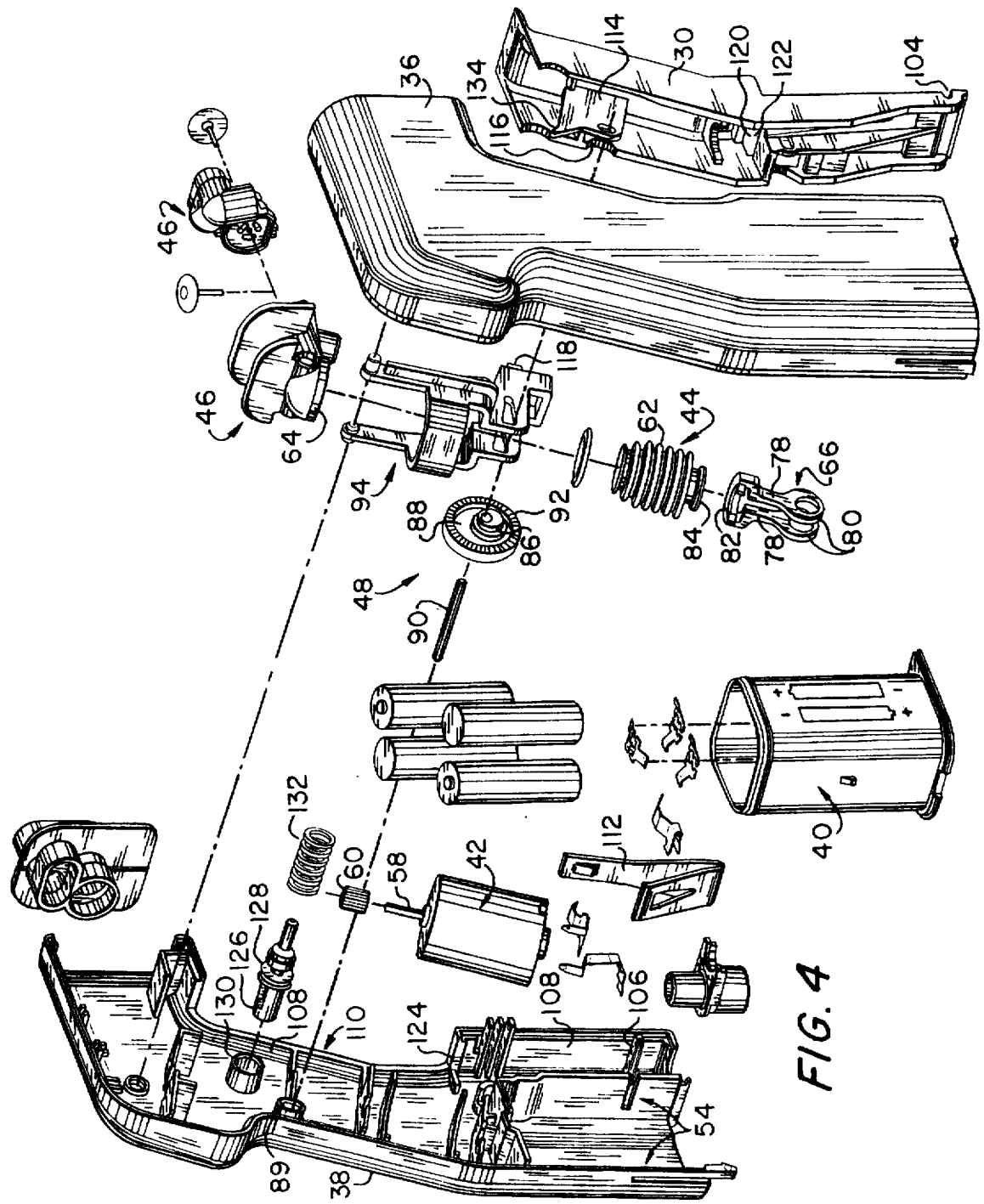
FIG. 4 is an exploded view of the components of the handpiece.
Figure 5C:
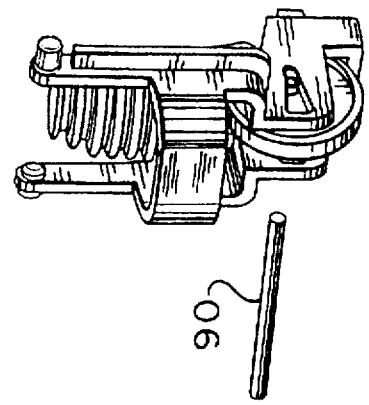
FIG. 5C is an illustration of a further stage of assembly of the components of the pump mechanism as shown in FIGS. 5A and 5B.
Figure 5B:
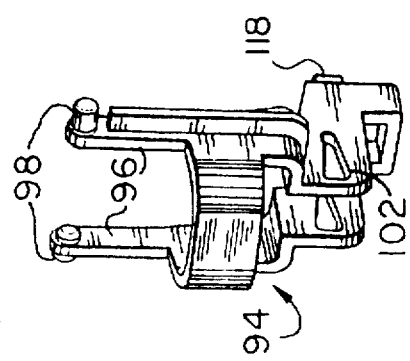
FIG. 5B is an exploded and partially assembled view of the pump components illustrated in FIG. 5A.
Figure 5A:
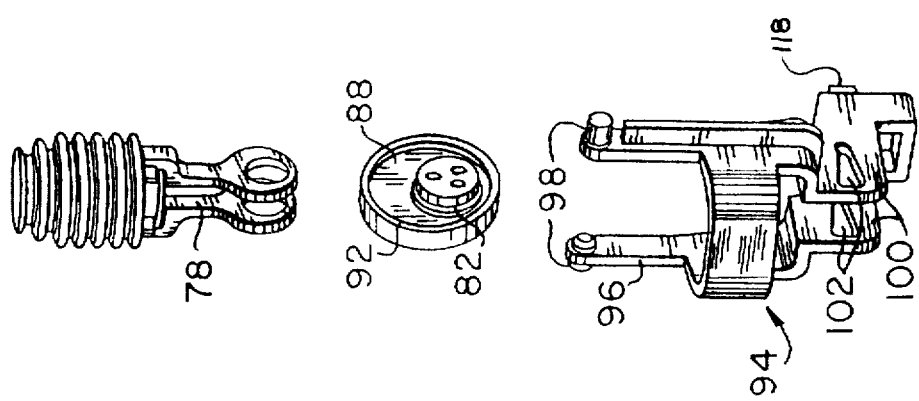
FIG. 5A is an exploded view of part of the pump mechanism.

The arrangement for disabling the electrical contacts while maintaining the trigger 30 in a depressed configuration may be appreciated from a consideration of FIGS. 1, 3 and 4. The arrangement includes a plastic, non-conductive locking pin 130 that is passed through a hole in the left side of the housing. The hole is oriented so that the pin 130 will pass between a pair of electrical contacts 138 that normally are closed by the depression of the trigger 30. The trigger 30 includes a slot 140 (FIGS. 3 and 4) through which the pin can protrude. The pin 130, although not shown in FIG. 3 emerges along the phantom line 142. Thus, the locking pin 130 enables the device to be configured with the trigger 30 depressed to maintain the internal tube 69 (not shown in FIGS. 3 or 4 for clarity) in an open configuration during sterilization, shipping and storage but while maintaining contacts that would normally be closed, in an open configuration.

From the foregoing it will be appreciated that the invention provides an improved pulsating irrigation device for use in surgical and other medical environments where pulsed lavage is desirable. The system is extremely simple in operation and set up, requiring only a simple plug-in connection to the irrigation liquid reservoir and connection of the section port to the suction source, if desired. All of the components, including the battery source are self-contained within the handpiece 20. A simplified, purely mechanical arrangement enables control of the output of the pump thereby avoiding more complex and more expensive arrangements that have been proposed and used in the prior art.

It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

What is claimed is:

1. A self-contained disposable pulsatile surgical irrigation device comprising:

a housing;

a trigger movably mounted to the housing;

a motor contained within the housing;

a battery contained within the housing for energizing the motor, the battery being electrically connectible to the motor by actuation of the trigger;

an electrical path defined within the housing between the motor and the battery and including an electrical switch within the housing, the switch being operatively associated with the trigger to selectively open or close the switch;

a linear fluid pump contained within the housing;

a mechanical drive train coupling the motor and the linear fluid pump, the drive train enabling the stroke of the linear fluid pump to be varied, thereby varying the output flow from the surgical irrigation device;

the trigger being mechanically connected to the drive train to effect said variation in stroke.

2. A device as defined in claim 1 wherein the linear pump comprises a bellows.

3. A device as defined in claim 2 further including a shaft and wherein the mechanical drive train includes an eccentric crank, the shaft extending through the crank;

the shaft being mounted within the housing for limited translational movement in a direction substantially perpendicular to the longitudinal axis of the shaft and along a direction that is generally along the axis of the bellows, whereby the amount of the bellows stroke is decreased by the amount of movement generally along the axis of the bellows, permitted by the shaft.

4. A device as defined in claim 3 further comprising:

a control member coupled to the trigger, the control member forming two elongated and tapered slots, the shaft extending through the slots, whereby the position of the trigger varies the position of the control member to control the extent to which the shaft is permitted said translational movement.

5. The device as defined by claim 1 further including a one-way valve system operatively associated with the linear fluid pump to effect one-way fluid flow in response to operation of the linear fluid pump.

6. The device as defined by claim 1 wherein the mechanical drive train includes a control member operatively connected to the trigger, the control member forming two elongated and tapered slots.

7. The device as defined by claim I wherein the interior of the housing forms a receptive socket and the device further includes a battery case, the battery case containing the battery and being slidably contained in the receptive socket.

8. The device as defined by claim 7 wherein the housing forms a flexible latching arm to removably secure the battery case within the receptive socket.

9. The device as defined by claim 1 further including an insulating lock pin removably connected between the electrical contacts.

10. A self-contained disposable pulsatile irrigation device comprising:

a housing;

a trigger movably mounted to the housing;

a motor contained within the housing;

a battery contained within the housing for energizing the motor, the battery being connectible to the motor by electrical contacts, the contacts being connectible between the battery and the motor by actuation of the trigger;

a linear fluid pump contained within the housing, the linear fluid pump having a longitudinal axis;

a drive train coupling the motor and the linear fluid pump, the drive train including a crank, the crank being rotatable about an axis, the axis of the crank being movable in a direction that is generally parallel to the longitudinal axis of the linear fluid pump;

the trigger being mechanically connected to the drive train to effect said movement of the axis in a direction that is generally parallel to the longitudinal axis of the linear fluid pump, thereby varying the output of fluid from the irrigation device.

11. The self-contained disposable pulsatile irrigation device as defined by claim 10 wherein the drive train includes a control member that forms a first elongated and tapered slot and a second elongated and tapered slot.

12. The self-contained disposable pulsatile irrigation device as defined by claim 11 further including a shaft extending through the crank, the shaft having a first end extending through the first slot and a second end extending through the second slot, the shaft being movable in a direction that is generally parallel to the longitudinal axis of the linear fluid pump.

13. The self-contained disposable pulsatile irrigation device as defined by claim 12 wherein the housing has an inner surface forming a first linear rail and a second linear rail, the first end of the shaft being within the first rail and the second end of the shaft being within the second rail.

14. The self-contained disposable pulsatile irrigation device as defined by claim 10 further comprising a one-way valve system operatively associated with the linear fluid pump to effect one-way fluid flow in response to operation of the linear fluid pump.

15. The self-contained disposable pulsatile irrigation device as defined by claim 10 wherein the linear fluid pump comprises a bellows.

16. The self-contained disposable pulsatile irrigation device as defined by claim 10 further including a connector socket in communication with the linear fluid pump for connecting a wand to the irrigation device.

17. The self-contained disposable pulsatile irrigation device as defined by claim 10 further including a lock pin removably connected between the electrical contacts.

18. The self-contained disposable pulsatile irrigation device as defined by claim 10 wherein the interior of the housing forms a receptive socket and the irrigation device further includes a battery case, the battery case containing the battery and being slidably contained in the receptive socket.

19. The self-contained disposable pulsatile irrigation device as defined by claim 18 wherein the housing forms a flexible latching arm to removably secure the battery case within the receptive socket.

* * * * *